United States Patent
Riehl

(10) Patent No.: US 7,104,947 B2
(45) Date of Patent: Sep. 12, 2006

(54) DETERMINING STIMULATION LEVELS FOR TRANSCRANIAL MAGNETIC STIMULATION

(75) Inventor: Mark Edward Riehl, Doylestown, PA (US)

(73) Assignee: Neuronetics, Inc., Malvern, PA (US)

( * ) Notice: Subject to any disclaimer, the term of this patent is extended or adjusted under 35 U.S.C. 154(b) by 322 days.

(21) Appl. No.: 10/714,741

(22) Filed: Nov. 17, 2003

(65) Prior Publication Data

US 2005/0107654 A1 May 19, 2005

(51) Int. Cl.
*A61N 1/00* (2006.01)
(52) U.S. Cl. ........................................................ 600/9
(58) Field of Classification Search .............. 600/9–15; 607/2

See application file for complete search history.

(56) References Cited

U.S. PATENT DOCUMENTS

| | | | |
|---|---|---|---|
| 3,683,923 A | 8/1972 | Anderson | 128/303.14 |
| 5,097,833 A | 3/1992 | Campos | 128/421 |
| 5,299,569 A | 4/1994 | Wernicke et al. | 607/45 |
| 5,655,534 A | 8/1997 | Ilmoniemi | 128/653.1 |
| 5,828,770 A | 10/1998 | Leis et al. | 382/103 |
| 5,923,417 A | 7/1999 | Leis | 356/141.1 |
| 6,061,644 A | 5/2000 | Leis | 702/153 |
| 6,179,771 B1 | 1/2001 | Mueller | 600/13 |

(Continued)

FOREIGN PATENT DOCUMENTS

EP    0 998 958 A3    5/2000

(Continued)

OTHER PUBLICATIONS

Nahas, Z. et al., "Safety and Feasibility of Repetitive Transcranial Magnetic Stimulation in the Treatment of Anxious Depression in Pregnancy: A Case Report", *J. Clin Psychiatry*, Jan. 1999, 60, 50-52.

(Continued)

*Primary Examiner*—John P. Lacyk
(74) *Attorney, Agent, or Firm*—Woodcock Washburn LLP

(57) ABSTRACT

Induced movement in a patient is detected and correlated with a TMS stimulating pulse so as to determine the patient's motor threshold stimulation level. Direct visual or audible feedback is provided to the operator indicating that a valid stimulation has occurred so that the operator may adjust the stimulation accordingly. A search algorithm may be used to direct a convergence to the motor threshold stimulation level with or without operator intervention. A motion detector is used or, alternatively, the motion detector is replaced with a direct motor evoked potential (MEP) measurement device that measures induced neurological voltage and correlates the measured neurological change to the TMS stimulus. Other signals indicative of motor threshold may be detected and correlated to the TMS stimulus pulses. For example, left/right asymmetry changes in a narrow subset of EEG leads placed on the forehead of the patient or fast autonomic responses, such as skin conductivity, modulation of respiration, reflex responses, and the like, may be detected. The appropriate stimulation level for TMS studies are also determined using techniques other than motor cortex motor threshold methods. For example, a localized ultrasound probe may be used to determine the depth of cortical tissue at the treatment site. When considered along with neuronal excitability, the stimulation level for treatment may be determined. Alternatively, a localized impedance probe or coil and detection circuit whose Q factor changes with tissue loading may be used to detect cortical depth.

48 Claims, 4 Drawing Sheets

U.S. PATENT DOCUMENTS

| | | | |
|---|---|---|---|
| 6,256,531 B1 | 7/2001 | Ilmoniemi et al. | 600/544 |
| 6,288,785 B1 | 9/2001 | Frantz et al. | 356/614 |
| 6,389,318 B1 | 5/2002 | Zarinetchi et al. | 607/61 |
| 6,463,328 B1 | 10/2002 | John | 607/45 |
| 6,484,059 B1 | 11/2002 | Gielen | 607/45 |
| 6,497,648 B1 | 12/2002 | Rey | 600/14 |
| 6,516,213 B1 | 2/2003 | Nevo | 600/424 |
| 6,516,288 B1 | 2/2003 | Bagne | 702/179 |
| 6,537,197 B1 | 3/2003 | Ruohonen et al. | 600/13 |
| 6,553,326 B1 | 4/2003 | Kirsch et al. | 702/65 |
| 6,560,490 B1 | 5/2003 | Grill et al. | 607/72 |
| 6,571,123 B1 | 5/2003 | Ives et al. | 600/544 |
| 6,625,563 B1 | 9/2003 | Kirsch et al. | 702/150 |
| 6,827,681 B1 | 12/2004 | Tanner et al. | 600/9 |
| 6,849,040 B1 | 2/2005 | Ruohonen et al. | 600/14 |
| 6,978,179 B1 | 12/2005 | Flagg et al. | 607/45 |
| 2002/0087201 A1 | 7/2002 | Firlik et al. | 607/45 |
| 2002/0091419 A1 | 7/2002 | Firlik et al. | 607/45 |
| 2003/0002315 A1 | 1/2003 | Tanner | 600/417 |
| 2003/0004392 A1 | 1/2003 | Tanner et al. | 600/9 |
| 2003/0023159 A1 | 1/2003 | Tanner | 600/417 |
| 2003/0050527 A1 | 3/2003 | Fox et al. | 600/13 |
| 2003/0065243 A1 | 4/2003 | Tanner | 600/9 |
| 2003/0073899 A1 | 4/2003 | Ruohonen et al. | 600/417 |
| 2003/0082507 A1 | 5/2003 | Stypulkowski | 434/262 |
| 2003/0088274 A1 | 5/2003 | Gliner et al. | 607/3 |
| 2003/0097161 A1 | 5/2003 | Firlik et al. | 607/72 |
| 2003/0125786 A1 | 7/2003 | Gliner et al. | 607/116 |
| 2003/0130706 A1 | 7/2003 | Sheffield et al. | 607/46 |
| 2004/0019370 A1 | 1/2004 | Gliner et al. | 607/48 |
| 2004/0153129 A1 | 8/2004 | Pless et al. | 607/62 |
| 2005/0021104 A1 | 1/2005 | DiLorenzo | 607/45 |
| 2005/0228209 A1 | 10/2005 | Schneider et al. | 600/13 |
| 2005/0256539 A1 | 11/2005 | George et al. | 607/2 |

FOREIGN PATENT DOCUMENTS

| | | |
|---|---|---|
| WO | WO 99/064884 | 12/1999 |
| WO | WO 01/97906 A2 | 12/2001 |
| WO | WO 02/032504 A2 | 4/2002 |
| WO | WO 02/072194 A2 | 9/2002 |
| WO | WO 02/08545 A1 | 10/2002 |
| WO | WO 02/085449 A2 | 10/2002 |
| WO | WO 02/089902 A2 | 11/2002 |
| WO | WO 02/094997 A2 | 11/2002 |
| WO | WO 03/035163 | 5/2003 |
| WO | WO 03/098268 A1 | 11/2003 |
| WO | WO 02/065768 A1 | 7/2005 |
| WO | WO 05/067610 A2 | 7/2005 |

OTHER PUBLICATIONS

Greene, YM., APA Meeting, Electromagnetic Stimulation Relieves Depression, http://HealthyPlace.com, May 17, 1999, 3 pages.

Baudewig, J. et al., "Functional MRI of Cortical Activations Induced by Transcranial Magnetic Stimulation(TMS)", *Brain Imaging-NeuroReport*, 2001, 12(16), 3543-3548.

Bohning, D.E. Ph.D. et al., "BOLD-fMRI Response to Single-Pulse Transcranial Magnetic Stimulation (TMS)", *Journal of Magnetic Resonance Imaging*, 2000, 11, 569-574.

Bohning, D.E. Ph.D. et al., "A Combined TMS/fMRI Study of Intensity-Dependant TMS over Motor Cortex", *Society of Biological Psychiatry*, 1999, 45, 385-394.

Bohning, D.E. et al., "A TMS Coil Positioning/Holding System for MR Image-Guided TMS Interleaved with fMRI", *Clinical Neurophysiology*, 2003, 114, 2210-2219.

George, M.S. et al., "A Controlled Trial of Daily Left Prefrontal Cortex TMS for Treating Depression", *Society of Biological Psychiatry*, 2000, 48, 962-970.

Grafman, J. Ph.D., "TMS as a Primary Brain Mapping Tool" *Transcranial Magnetic Stimulation in Neuropsychiatry*, 2000, 115-140.

Lisanby, S.H. et al., "Sham TMS: Intracerebral Measurement of the Induced Electrical Field and the Induction of Motor-Evoked Potentials", *Society of Biological Psychiatry*, 2001, 49, 460-463.

Lorberbaum, J.P., M.D. et al., "Safety Concerns of TMS", *Transcranial Magnetic Stimulation in Neuropsychiatry*, 2000, 141-161.

Loo, C.K. et al., "Transcranial Magnetic Stimulation (TMS) in Controlled Treatment Studies: Are Some "Sham" Forms Active?", *Society of Biological Psychiatry*, 2000, 47,325-331.

Nahas, Z. et al., "Left Prefrontal Transcranial Magnetic Stimulation(TMS) Treatment of Depression in Bipolar Affective Disorder: A Pilot Study of Acute Safety and Efficacy", *Bipolar Disorders*, 2003, 5, 40-47.

Nahas, Z. et al., "Unilateral Left Prefrontal Transcranial Magnetic Stimulation(TMS) Produces Intensity-Dependent Bilateral Effects as Measured by Interleaved BOLD fMRI", *Society of Biological Psychiatry*, 2001, 50, 712-720.

Pridmore, S., "Substitution of Rapid Transcranial Magnetic Stimulation Treatments for Electroconvulsive Therapy Treatments in a Course of Electroconvulsive Therapy", *Depression and Anxiety*, 2000, 12, 118-123.

Ruohonen, J., "Electroencephalography Combined with TMS", BioMag Laboratory, Helsinki University Central Hospital, http://www.biomag.helsinki.fi/tms/TMSEEG.html, Oct. 6, 1999, 22 pages.

US 7,104,947 B2

DETERMINING STIMULATION LEVELS FOR TRANSCRANIAL MAGNETIC STIMULATION

FIELD OF THE INVENTION

The present invention relates to the field of electrical brain stimulation for the treatment of various illnesses. In particular, the invention relates to a method and apparatus for determining stimulation signal levels for applying electrical brain stimulation to a patient.

BACKGROUND OF THE INVENTION

Current methods of determining motor threshold (MT) position and stimulation levels for transcranial magnetic stimulation (TMS) studies rely on visual observation and interpretation of induced twitching of the thumb (i.e. abductor pollicis brevis) or by electromyography (EMG), which involves observation and interpretation of electrical response waveforms. In particular, a common method is to stimulate the motor cortex, observe thumb twitch or observe when the desired EMG signal exceeds a threshold value (i.e. motor evoked potential, MEP) as the stimulation level is manually adjusted. Both techniques are time consuming and highly dependent upon the skills and training of the practitioner. A more automated technique is desired that is not so operator dependent and time consuming. Such a technique should ideally provide simple feedback to the operator or may be used to close the loop to automate the motor threshold position determination process.

It would be advantageous to more directly determine desired levels for stimulating non-motor areas of the brain (e.g. prefrontal cortex); however, such techniques have not yet been developed. Direct measurement of evoked potential for non-motor areas using EMG techniques has been proposed by Sarah Lisanby, M.D. Unfortunately, direct measurement of evoked potential is not straight-forward since neurons that are directly stimulated are not readily accessible with non-invasive techniques. Functional magnetic resonance imaging (fMRI) or positron emission tomography may be used to observe levels of neuronal stimulation, but these methods are expensive, would require TMS procedures to be performed at a facility with this equipment, and are logistically impractical for routine clinical TMS therapy. Indirect methods such as observation and interpretation of electroencephalogram (EEG) signals may be possible and are generally described herein.

Numerous search algorithms to determine the optimal stimulation level have also been proposed and tested clinically. For example, a procedure often used in TMS research estimates the motor threshold at a stimulus strength where 5 successes are observed within 10 stimuli. Another approach estimates the arithmetic mean of an upper threshold (smallest stimulus strength with 10 successes in 10 trials) and a lower threshold (largest stimulus strength with no success in 10 trials). Professor Friedemann Awiszus (Magdeburg, Germany) describes another search strategy for threshold estimation called the PEST (parameter estimation by sequential testing) algorithm in a publication titled "TMS and Threshold Hunting." The PEST algorithm uses adaptive threshold hunting to estimate the threshold continuously throughout the stimulus sequence where the stimulus strength that is to be used for the next stimulus is calculated from the information obtained from the previous stimuli.

The block diagram of FIG. 1 shows the typical motor threshold level determination procedure used today. In this case the operator 10 operates a TMS stimulator 20 that provides pulses to a stimulation magnet 30 for application of TMS signals to a patient 40. The operator 10 receives direct visual feedback from the patient 40 or from an EMG display (not shown). The stimulation level and/or position is then adjusted manually by the operator 10 and the process repeated until a level is attained where half of the stimulation pulses result in a valid detected movement of the thumb. This approach can be augmented by employing an offline search algorithm 50, such as the PEST algorithm, to aid in selecting stimulation values based on prior responses. Use of the PEST algorithm is reflected by the diagram in prior art FIG. 2.

It is known to monitor patient movement to detect evidence of seizure activity. For example, Gliner discloses in U.S. Patent Publication No. US 2003/0074032 A1 a neural stimulation system that uses a sensing unit to detect evidence of seizure or other collateral neural activity in response to an applied neural stimulation. The sensing unit may be an EEG monitoring device, a cerebral blood flow (CBF) monitor, a neural tissue oxygenation analysis device, or an electromyography device. In one embodiment, the monitoring device may also comprise a set of motion detectors, strain gauges, and/or accelerometers configured to detect or monitor one or more types of patient movements that may be indicative of seizure activity. However, Gliner does not suggest how such a system may be used to detect motor threshold positions and levels and does not suggest correlating induced movement in the patient with a stimulation pulse to find the motor threshold position. On the contrary, the Gliner system stops the application of neural stimulation when a potential seizure or other collateral neural activity is detected. Moreover, Gliner is focused on seizure detection/prevention which is a very different purpose and involves detecting very different signal characteristics than proposed in accordance with the present invention. In the present application, the inventor is interested in detecting and observing "normal" levels of nerve stimulation, even though the stimulation is induced with a magnetic field. Seizures are a different phenomenon that typically occur at very much higher levels of magnetic stimulation (e.g. >2 times the MT level).

None of the prior art techniques known to the inventor suggests how to directly detect induced physical movement and how to correlate detected induced movement with TMS stimulation levels in order to determine TMS treatment stimulation levels or motor threshold. Prior art techniques do not describe methods of separately determining cortical depth and levels of neuronal excitability for the purpose of setting TMS stimulation levels. The prior art also does not teach techniques of determining TMS stimulation levels by observation and analysis of indirect signals such as EEG and its derivatives. The present invention addresses these needs in the art.

SUMMARY OF THE INVENTION

The present invention addresses the above-mentioned needs in the art by providing a means to detect induced movement or other activity in the patient and to correlate such movement or activity with a TMS stimulating pulse so as to determine the proper stimulation level at which to treat the patient, i.e., typically the motor threshold (MT) level. For example, the present invention may use an adaptive filter or correlator that is trainable by operator confirmation of a valid stimulation and means of providing direct visual or audible feedback to the operator that a valid stimulation has occurred.

In a first embodiment of the invention, motion detectors are used to detect specific patient movements and the motion detection outputs are provided via a feedback path to the TMS stimulator. The feedback path includes a valid motion stimulation detector that correlates the detected movement to the TMS stimulating pulse using, for example, a correlator or an adaptive filter. It is important to differentiate patient-initiated movement from stimulation-induced movement; therefore, correlation with the stimulation signal and isolation of specific muscle group movement is needed to specify when a true TMS stimulation has occurred. In the simplest implementation, the operator of the TMS stimulation equipment observes the output of the valid motion detector and enters whether a successful stimulation has occurred (or not) to an algorithm such as PEST which assists in computing the next stimulation level to try. A series of stimulation values are tried until they converge to the MT value which is then used to set the treatment stimulation level. In another variation of the invention, the valid motion detection signal may be directly provided to the algorithm without user intervention.

In a second embodiment of the invention, the motion detectors are replaced with direct motor evoked potential (MEP) measurement devices that measure induced neurological voltage and correlate the measured neurological change to the TMS stimulus. An EMG system is used to detect a waveform that is correlated with a valid stimulus. As in the first embodiment, a feedback loop (with or without an operator) is used to seek convergence to the motor threshold value.

In a third embodiment of the invention, a signal is detected other than one caused by physical motion and that also has a strong correlation to specific focal stimulation of target areas of the motor cortex. For example, left/right asymmetry changes in a narrow subset of EEG signals derived from electrodes placed on the forehead of the patient (or elsewhere), or fast autonomic responses, such as skin conductivity, modulation of respiration, reflex responses, and the like, may be detected. In another variation of the invention, the indirect signals may be correlated to stimulation of non-motor areas of the brain such as the prefrontal cortex.

In a fourth embodiment of the invention, the appropriate stimulation level for TMS studies is determined using techniques other than motor cortex motor threshold methods. There are two parameters that affect proper setting of TMS stimulation levels: cortical depth and level of neuronal excitability. Desired stimulation is proportional to the product of these parameters. This embodiment separately determines each of these two parameters. A localized ultrasound probe may be used to determine the depth of cortical tissue at the treatment site. Alternatively, a localized and specifically designed probe may be used to detect impedance changes or filling factor differences when the probe is placed on the scalp at the desired treatment site. Such a probe may be constructed using a tuned coil and detection circuit that is sensitive to loading differences encountered when different biological tissue is placed in its proximity. The probe may be calibrated by observing impedance or Q factor (i.e. frequency*inductance/resistance) at a location where cortical depth is known from other methods such as ultrasound or standard motor threshold methods. Linearity and sensitivity must be determined by conducting these observations over a range of tissue depths, locations and subjects. An alternative variation of this probe is to transmit a radiofrequency (RF) pulse through this tuned circuit to the patient's head at the proposed stimulation site and observe the absorbed power compared to that at a known cortical depth. These methods rely on loading differences between cerebral spinal fluid and cortical tissue and therefore require a high degree of sensitivity and appropriate calibration. Once the cortical depth is determined the neuronal excitability may be estimated by a number of standard neurological and/or psychological measures, including but not limited to EEG signal analysis (or subset thereof), measurement of autonomic response times, and depth of awareness measures (e.g. Aspect Medical, Inc. bispectral index or BIS™).

BRIEF DESCRIPTION OF THE DRAWINGS

The above-mentioned features and advantages of the invention will be apparent from the following detailed description in conjunction with the drawings, of which.

DETAILED DESCRIPTION OF ILLUSTRATIVE EMBODIMENTS

Figure 1:
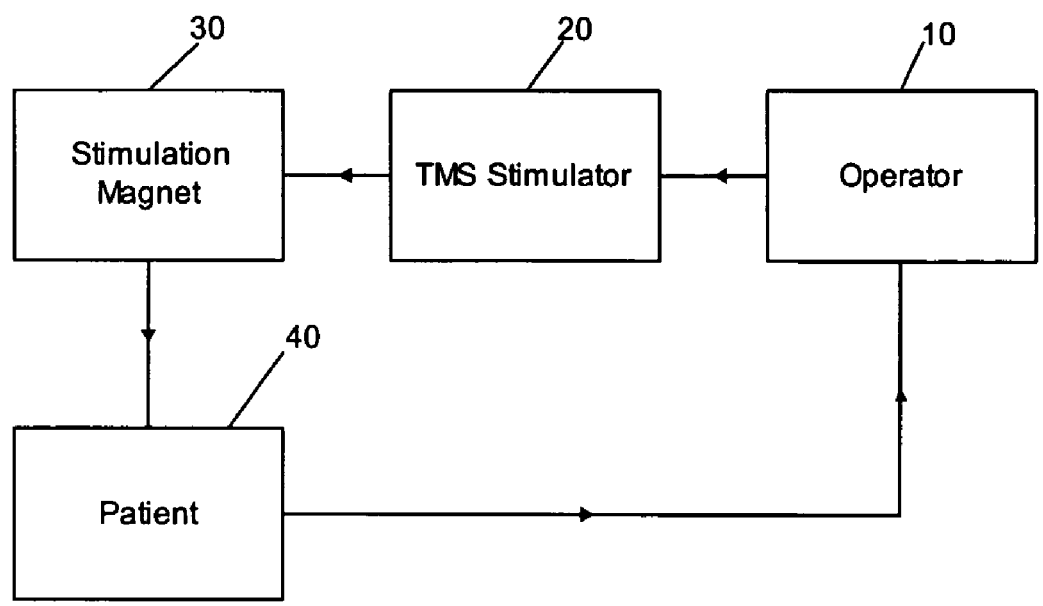
FIG. 1 illustrates a conventional motor threshold level determination procedure.

A detailed description of exemplary embodiments of the present invention will now be described with reference to FIGS. 3 and 4. Although this description provides detailed examples of possible implementations of the present invention, it should be noted that these details are intended to be exemplary and in no way delimit the scope of the invention.

Prior to TMS, the patient's motor threshold (MT) position is determined and the stimulation position is determined in reference to the MT position. The magnetic flux density, B, produced by the TMS therapy coil is adjusted with the coil positioned at the MT position in order to determine the MT stimulation level. This level is variable from patient to patient or over time for a given patient. Therefore, this procedure may have to be repeated. A simple and repeatable process to facilitate setting the MT stimulation level is thus advantageous in the clinical TMS procedure. The TMS therapy stimulation level is set as a relative percent of this MT value, so an accurate determination of MT level is important for systematic and safe TMS therapy.

Motion Detection Methods

The motor threshold position for TMS therapy is the coil position over the motor cortex at which the applied stimulus causes physical movement or twitching of the abductor pollicis brevis muscle (i.e. thumb) on the contralateral hand. Conventional detection methods use the operator's observations and/or measurement of electrical response waveforms (i.e. EMG). A first embodiment of the present invention shown in FIG. 3 improves upon such techniques by providing a motion detector including sensors 60 to detect patient movement (as opposed to relying upon operator observations. Sensors 60 provide motion detection outputs in a feedback path to the TMS stimulator 20 via signal processor 70, valid motion stimulation detector 80 and search algorithm 50 as shown in FIG. 3.

Several technologies that may be used for the motion detector 60 include:
1) Physical motion sensors (e.g. LVDT, strain gauge, linear potentiometer, digital encoder);
2) Optical motion sensors (e.g. laser-based distance measurement devices);
3) Ultrasonic motion sensors (e.g. reflection delay devices); and
4) RF motion sensors (e.g. interferometers).

Figure 2:
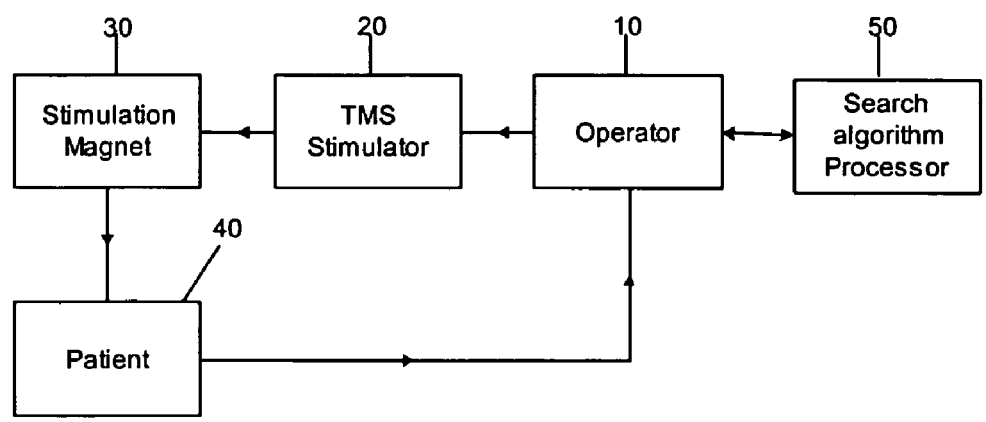
FIG. 2 illustrates the use of the PEST algorithm with the procedure of FIG. 1.

Any of these sensor types may be used to produce a signal that is processed by signal processor 70 to eliminate noise and the like through techniques such as quadrature detection, filtering and signal averaging. The resulting signal is fed to the "valid motion stimulation" detector 80 including, for example, a correlator or an adaptive filter that is also given the timing of the stimulation pulse from TMS stimulator 20 to determine whether the detected movement is a valid TMS induced motion or the result of incidental patient initiated movement. Detection of the valid stimulus may then be reported directly to the operator (visual signal, audible signal, or displayed message) as in the prior art embodiments of FIGS. 1 and 2 (see dashed line 85). Alternatively, as shown in FIG. 3, the signal may be provided to a processor 50 that operates a search algorithm such as PEST to determine the next stimulation level to try and to indicate convergence. The output of this algorithm may then be provided to the operator 10 who sets the new value for the next iteration.

Figure 3:
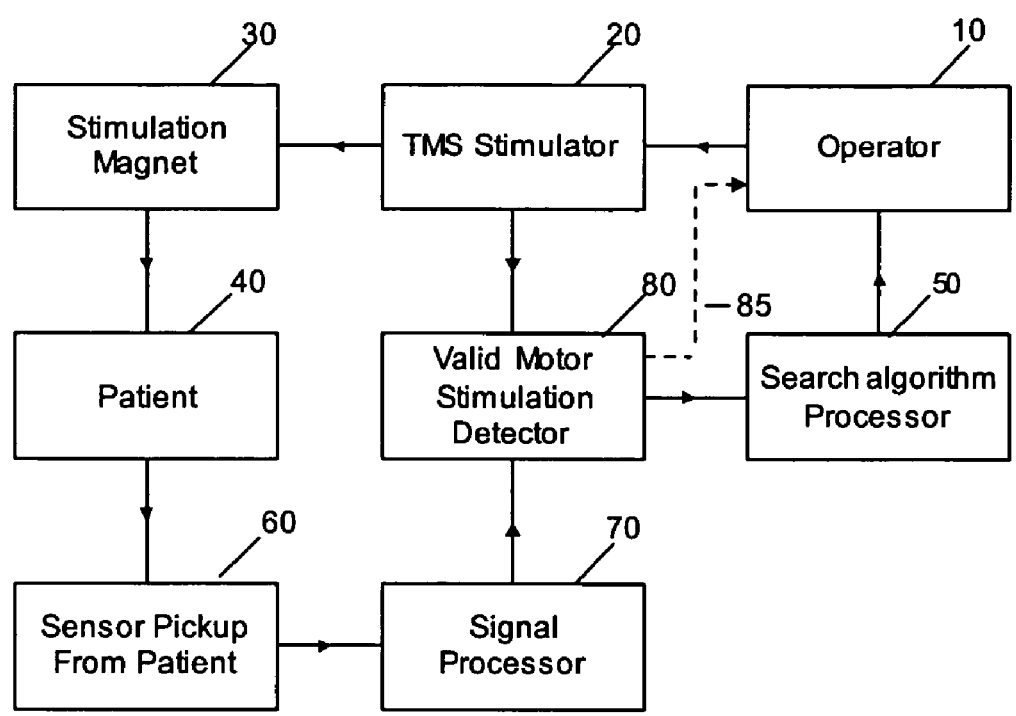
FIG. 3 illustrates an embodiment of the invention using a motion detector to detect patient movement for correlation to the TMS stimulation pulse.
Figure 4:
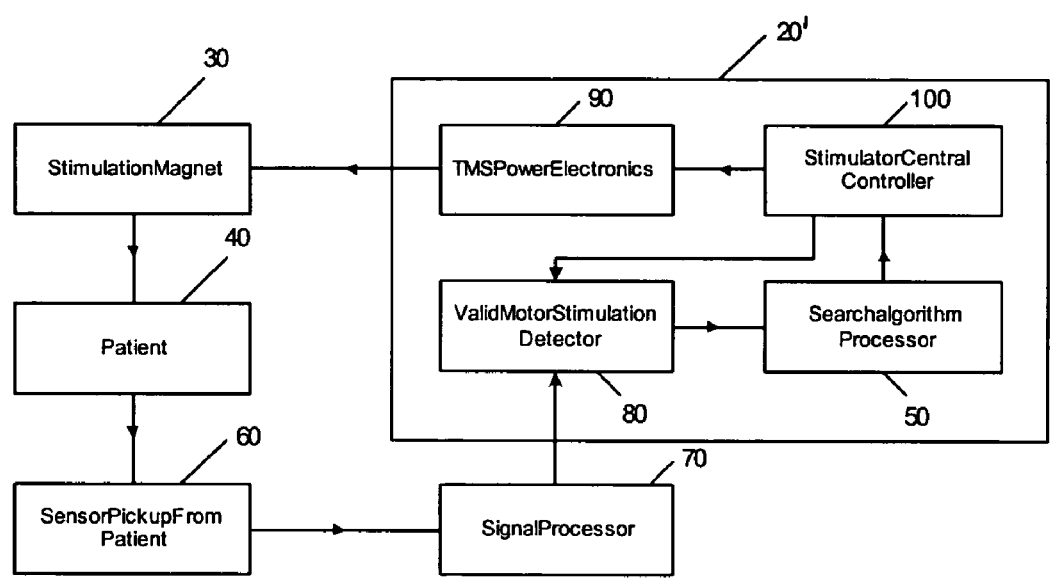
FIG. 4 illustrates a further embodiment in which the operator is removed from the feedback loop of the FIG. 3 embodiment.

FIG. 4 illustrates a further embodiment in which the operator 10 is removed from the feedback loop. In this embodiment, the TMS stimulator 20 of FIG. 3 is provided with sufficient intelligence and processing power that it may incorporate the valid motor stimulation detector 80 and the search algorithm processor 50. The enhanced TMS stimulator is identified as element 20' in FIG. 4. As shown, the enhanced TMS stimulator 20' may also include TMS power electronics 90 for providing the stimulation signal to the stimulation magnet 30 as well as a stimulator central controller 100 that is responsive to the search algorithm 50 to generate control signals that seek convergence to find the motor threshold value. Another variation on the motion sensor method proposed here is the use of more than one sensor 60 at more than one location so that motion can be narrowed to a particular muscle group that moved in response to a stimulation signal. This is important since stimulation of certain portions of the motor cortex results in movement of large muscle groups, such as the arm or whole hand. Proper determination of the TMS motor threshold requires isolation of specific muscles so that the setting of the level is repeatable from session to session.

Evoked Potential and EMG Detection Methods

Other proposed aspects of the invention include replacing motion detection sensors 60 of FIGS. 3 and 4 with direct motor evoked potential (MEP) measurement devices that measure an induced neurological voltage and correlate the measured neurological voltage to the TMS stimulus. This can be done by using an EMG system to detect a waveform and using a signal processing algorithm or simple threshold detector to determine a valid stimulus. This technique has been widely used by many researchers, but it requires a sophisticated user and equipment to avoid problems with signal interpretation. Use of this method to detect a valid signal and using it in a closed loop control scheme has been proposed by the developers of PEST. However, specific details to make such an implementation practical have not been communicated in known prior art. The present inventor has recognized that a successful implementation requires allowing for capacitor charging and/or discharging times after the target stimulation has been set by the controller. A delay is required or, alternately, early responses can be ignored. Because of the high degree of artifact in EMG signals requiring significant operator interaction to set up the equipment correctly and to successfully detect a valid stimulus from a highly varied and complex waveform, MEP and EMG are not used in preferred embodiments of the invention.

The MEP embodiment of the invention further recognizes a variation on the EMG approach that includes setting the TMS stimulation level without using the motor cortex. Instead, the TMS coil associated with the stimulation magnet 30 is positioned and the stimulation level is adjusted both by indirectly measuring the evoked potential or the corresponding change to the EEG waveforms when the dorsolateral prefrontal cortex (DLPFC) is stimulated. The latter form would be the ideal approach for TMS since it avoids the motor cortex motor threshold procedure entirely. Studies that correlate EEG waveforms to DLPFC stimulation levels have not been thoroughly done at this time. However, the literature recognizes changes in EEG waveforms and quantitative EEG measures corresponding to neurological conditions, such as major depression.

Non-Motion Detection Methods

Another embodiment of the invention includes the detection of a signal other than one caused by physical motion (i.e. thumb twitching) which also has a reasonable and strong correlation to stimulation of the motor cortex. The following possible signals are proposed:
a) Left/right asymmetry changes in a narrow subset of EEG leads placed preferably on the forehead of the patient; and
b) Fast autonomic responses that are directly detectable (e.g. skin conductivity, modulation of respiration, reflex responses).

In such an embodiment, the sensors 60 of FIGS. 3 and 4 would be replaced by EEG detection devices and/or by fast autonomic response detectors that measure skin conductivity, modulation of respiration, reflex responses, and the like. These are signals typically used in a polygraph. Skin conductivity is measured with a pair of electrodes in contact with the skin and connected to a calibrated ohmmeter. Respiration can be measured with an expandable bellows placed around the subject's chest. The bellows is attached to a pressure sensor or (rarely) a flowmeter to detect a respiration signal. This signal is electronically processed to determine periodicity which is the respiration rate. The rate can be calculated as a rolling average which may be time correlated with a cortical stimulation. Reflex responses could be measured with motion sensors similar to those described above.

Non-Motor Cortex Methods

There are potentially other radically different methods of determining the appropriate stimulation level for TMS studies other than the motor cortex motor threshold methods. These methods rely on the determination of two parameters: cortical depth and neuronal excitability. Several means for determining depth are described here. One such means is using a localized ultrasound probe (or separate angled transmit and receive transducers) to determine depth of cortical tissue at the treatment site. This measurement then may be correlated to the motor cortex methods discussed above to test accuracy and repeatability of the method. For example, motor threshold may be determined for a particular patient using the visual detection of thumb twitch. The cortical depth can then be performed at the same site using an ultrasound (or other) technique. A neuronal excitability index, NE, can be calculated as: NE=MT/Depth. The depth can now be determined at the treatment site and the MT value calculated as MT=NE*Depth. This may be more accurate than assuming the MT is the same for MT and therapy sites, as is done in most studies at this time. Alternatively, a NE may be developed using other means such as EMG, or cognitive assessment tools. Once this technique has been calibrated against a standard MT method, depth can be measured and multiplied by the NE to get MT.

Another alternative technology to measure cortical depth is the use of a localized impedance probe or a coil and detection circuit whose Q factor changes with tissue loading. This technique operates on the principle that coil loading (or alternatively RF power absorption) varies with cortical depth. This approach may require transmission of low power RF signals and determining attenuation levels or reflections from the cortical surface, or just simply doing a very accurate measurement of coil loading. In addition, this approach may be applied at multiple sites to determine a baseline or variations from the motor cortex area to the TMS therapy area. For example, depth may again be combined with a NE as described above to determine MT.

Alternatively, a localized and specifically designed probe may be used to detect impedance changes or filling factor differences when the probe is placed on the scalp at the desired treatment site. Such a probe may be constructed using a tuned coil and detection circuit that is sensitive to loading differences encountered when different biological tissue is placed in its proximity. The probe may be calibrated by observing impedance or Q factor (i.e. frequency*inductance/resistance) at a location where cortical depth is known from other methods such as ultrasound or standard motor threshold methods. Linearity and sensitivity must be determined by conducting these observations over a range of tissue depths, locations and subjects. An alternative variation of this probe is to transmit a radiofrequency (RF) pulse through this tuned circuit to the patient's head at the proposed stimulation site and observe the absorbed power compared to that at a known cortical depth. These methods rely on loading differences between cerebral spinal fluid and cortical tissue and therefore require a high degree of sensitivity and appropriate calibration. Once the cortical depth is determined the neuronal excitability may be estimated by a number of standard neurological and/or psychological measures, including but not limited to EEG signal analysis (or subset thereof), measurement of autonomic response times, and depth of awareness measures (e.g. Aspect Medical, Inc. bispectral index or BIS™).

It is to be understood that the foregoing illustrative embodiments have been provided merely for the purpose of explanation and are in no way to be construed as limiting of the invention. Words used herein are words of description and illustration, rather than words of limitation. In addition, the advantages and objectives described herein may not be realized by each and every embodiment practicing the present invention. Further, although the invention has been described herein with reference to particular structure, materials and/or embodiments, the invention is not intended to be limited to the particulars disclosed herein. Rather, the invention extends to all functionally equivalent structures, methods and uses, such as are within the scope of the appended claims. Those skilled in the art, having the benefit of the teachings of this specification, may affect numerous modifications thereto and changes may be made without departing from the scope and spirit of the invention.

The invention claimed is:

1. A system for determining a patient's motor threshold level for stimulation of the patient's motor cortex for use in transcranial magnetic stimulation of the patient, comprising:
   a stimulation magnet that generates transcranial magnetic stimulation (TMS) fields for application to the patient;
   a transcranial magnetic stimulation (TMS) stimulator that outputs stimulation signals for causing said stimulation magnet to generate TMS fields;
   a sensing device that detects a change in the patient's condition indicative of motor threshold during application of the TMS fields and outputs sensed signals; and
   a detector responsive to said stimulation signals and said sensed signals to determine if a detected change in the patient's condition indicative of motor threshold is induced by a stimulation signal and to output a correlation signal indicative of correlation of the detected change and the stimulation signal.

2. A system as in claim 1, further comprising a signaling device that signals an operator of the TMS stimulator whether the detected change and the stimulation signal were correlated.

3. A system as in claim 1, further comprising a search algorithm responsive to a correlation output of said detector, said search algorithm determining a next stimulation signal to be applied to said stimulation magnet by said TMS stimulator so as to cause convergence of said TMS fields to a motor threshold level.

4. A system as in claim 3, further comprising a stimulator controller responsive to an output of said search algorithm to generate a stimulator control signal for application to said TMS stimulator so as to cause said TMS stimulator to generate, without operator intervention, the next stimulation signal to be applied to said stimulation magnet.

5. A system as in claim 4, wherein said TMS stimulator includes said detector, said search algorithm and said stimulator controller.

6. A system as in claim 1, wherein the sensing device comprises a motion detector that detects motion of the patient or a specific muscle group of the patient induced by application of a TMS field.

7. A system as in claim 6, wherein the motion detector includes at least one of physical motion sensors, optical motion sensors, ultrasonic motion sensors, and radiofrequency motion sensors.

8. A system as in claim 1, wherein the sensing device comprises direct motor evoked potential (MEP) measurement devices that measure induced neurological voltage in the patient as a result of application of a TMS field to the patient.

9. A system as in claim 8, wherein the MEP measurement devices comprise an electromyography system that measures induced neurological voltage in the patient and said detector comprises a signal processing system that correlates a measured induced neurological voltage with a stimulation signal from said TMS stimulator.

10. A system as in claim 8, wherein the TMS field is applied to the dorsolateral prefrontal cortex (DLPFC) of the patient and MEP measurement devices measure a resulting evoked potential caused by stimulation of the DLPFC.

11. A system as in claim 1, wherein the sensing device comprises EEG leads placed on a forehead of the patient so as to measure left/right asymmetry changes in a subset of the EEG leads.

12. A system as in claim 1, wherein the sensing device comprises an autonomic response detector that detects autonomic responses correlated with stimulation of the motor cortex.

13. A system as in claim 12, wherein said autonomic response detector comprises at least one of a skin conductivity detector, a respiration modulation detector, and a reflex response detector.

14. A system as in claim 1, wherein said detector comprises at least one of a correlator and an adaptive filter that correlates detected change in the patient's condition indicative of motor threshold with the stimulation signal to determine whether the detected change in the patient's condition indicative of motor threshold was induced by application of the TMS field generated in response to the stimulation signal.

15. A system for determining an appropriate stimulation location for transcranial magnetic stimulation of a patient, comprising:
a stimulation magnet that generates transcranial magnetic stimulation (TMS) fields for application to the patient;
a transcranial magnetic stimulation (TMS) stimulator that outputs stimulation signals for causing said stimulation magnet to generate TMS fields;
a probe that measures depth of cortical tissue at a treatment site and outputs a measurement signal;
a detector responsive to said stimulation signals and said measurement signal to determine neuronal excitability; and
a processor that determines cortical depth at a therapy location and calculates a treatment stimulation level at the therapy location using a neuronal excitability and the measured cortical depth of cortical tissue.

16. A system as in claim 15, wherein said processor calculates the treatment stimulation level (MT) as a product of a neuronal excitability index (NE) and the measured cortical tissue depth (Depth) at the treatment site, where MT=NE*Depth.

17. A system as in claim 15, wherein the probe is a localized ultrasound probe that measures attenuation levels or reflections from a cortical surface.

18. A system as in claim 17, wherein the probe comprises angled transmit and receive transducers that measure attenuation levels or reflections of RF signals from a cortical surface.

19. A system as in claim 15, wherein the probe is a localized impedance probe whose Q factor changes with tissue loading so as to detect cortical depth.

20. A system as in claim 15, wherein the probe comprises a coil and detection circuit having a Q factor that changes with tissue loading so as to detect cortical depth.

21. A method of determining a patient's motor threshold of the patient's motor cortex for use in transcranial magnetic stimulation of the patient, comprising the steps of:
generating stimulation signals for causing a stimulation magnet to generate transcranial magnetic stimulation (TMS) fields;
generating TMS fields in response to said stimulation signals for application to the patient;
detecting a change in the patient's condition indicative of motor threshold during application of the TMS fields and outputting sensed signals; and
determining if a detected change in the patient's condition indicative of motor threshold is induced by a stimulation signal and outputting a correlation signal indicative of correlation of the detected change and the stimulation signal.

22. A method as in claim 21, further comprising the step of signaling an operator of TMS stimulation equipment whether the detected change and the stimulation signal were correlated.

23. A method as in claim 21, further comprising the step of determining a next stimulation signal to be applied to said stimulation magnet by said TMS stimulator using a search algorithm so as to cause convergence of said TMS fields to a motor threshold level.

24. A method as in claim 23, further comprising the step of generating a stimulator control signal for application to said TMS stimulator so as to cause said TMS stimulator to generate, without operator intervention, the next stimulation signal to be applied to said stimulation magnet.

25. A method as in claim 21, wherein the detecting step comprises a step of delaying after a change in stimulation level to allow a stimulating capacitor to charge and/or discharge to achieve a selected stimulation level.

26. A method as in claim 21, wherein the detecting step comprises a step of detecting motion of the patient induced by application of a TMS field.

27. A method as in claim 26, comprising the additional step of measuring motion of the patient at multiple treatment sites to isolate muscle groups for which motion is induced by application of said TMS field.

28. A method as in claim 21, wherein the detecting step comprises the step of measuring induced neurological voltage in the patient as a result of application of a TMS field to the patient.

29. A method as in claim 28, wherein the measuring step comprises the step of measuring induced neurological voltage in the patient using an electromyography system and said determining step comprises the step of correlating a measured induced neurological voltage with a stimulation signal.

30. A method as in claim 29, wherein the TMS fields generating step comprises the step of applying the TMS fields to the dorsolateral prefrontal cortex (DLPFC) of the patient and said measuring step comprises the step of measuring a resulting evoked potential caused by stimulation of the DLPFC.

31. A method as in claim 21, wherein the detecting step comprises the steps of placing EEG leads on a forehead of the patient and measuring left/right asymmetry changes in a subset of the EEG leads.

32. A method as in claim 21, wherein the detecting step comprises the step of detecting autonomic responses of the patient and said determining step comprises the step of correlating autonomic responses with stimulation of the motor cortex.

33. A method as in claim 21, wherein said determining step comprises the steps of using at least one of a correlator and an adaptive filter to correlate detected change in the patient's condition indicative of motor threshold with the stimulation signal and determining whether the detected change in the patient's condition indicative of motor threshold was induced by application of the TMS field generated in response to the stimulation signal.

34. A method of determining an appropriate stimulation level for transcranial magnetic stimulation of a patient, comprising the steps of:

generating stimulation signals for causing a stimulation magnet to generate transcranial magnetic stimulation (TMS) fields;

generating TMS fields in response to said stimulation signals for application to the patient;

measuring a depth of cortical tissue at a treatment site and outputting a measurement signal; and determining if a measured depth of cortical tissue at the treatment site correlates to a treatment level determined using motor threshold measurement at the motor cortex.

35. A method as in claim 34, further comprising the step of determining neuronal excitability.

36. A method as in claim 35, wherein said determining step comprises the step of calculating a treatment stimulation level at the treatment site using the determined neuronal excitability and measured cortical tissue depth at the treatment site.

37. A method as in claim 36, wherein said calculating step comprises the step of calculating the treatment stimulation level (MT) as a product of a neuronal excitability index (NE) and the measured cortical tissue depth (Depth) at the treatment site, where MT=NE*Depth.

38. A method as in claim 34, wherein the measuring step comprises the step of measuring attenuation levels or reflections from a cortical surface.

39. A method as in claim 38, wherein the measuring step comprises the step of measuring attenuation levels or reflections of RF signals from a cortical surface using angled transmit and receive transducers.

40. A method as in claim 34, wherein the measuring step comprises the step of measuring cortical depth using a localized impedance probe whose Q factor changes with tissue loading to detect cortical depth.

41. A method as in claim 34, wherein the measuring step comprises the step of measuring cortical depth using a coil and detection circuit that measure cortical depth by accurately measuring loading of said coil during application of a TMS field in a region including the coil.

42. A method as in claim 34, wherein the measuring step comprises the step of measuring impedance changes or filling factor differences when an impedance probe is placed at the treatment site.

43. A method as in claim 42, comprising the further steps of transmitting a radiofrequency pulse to the treatment site and observing absorbed power compared to absorbed power at a known cortical depth.

44. The system of claim 1, wherein the stimulation magnet is coil-shaped.

45. The system of claim 1, wherein the stimulation magnet comprises a core.

46. The system of claim 1, wherein the TMS fields are capable of accomplishing magnetic seizure therapy.

47. The method of claim 21, wherein the TMS fields are capable of accomplishing magnetic seizure therapy.

48. The method of claim 34, wherein the TMS fields are capable of accomplishing magnetic seizure therapy.

* * * * *